(12) United States Patent
Turovskiy et al.

(10) Patent No.: US 6,280,432 B1
(45) Date of Patent: Aug. 28, 2001

(54) CLIP-ON ACCESS PORT AND METHODS OF USE

(75) Inventors: Roman Turovskiy, San Francisco; Yue-Teh Jang, Fremont, both of CA (US)

(73) Assignee: Embol-X, Inc., Mountain View, CA (US)

( * ) Notice: Subject to any disclaimer, the term of this patent is extended or adjusted under 35 U.S.C. 154(b) by 0 days.

(21) Appl. No.: 09/369,058

(22) Filed: Aug. 4, 1999

(51) Int. Cl.⁷ ................................................. A61M 25/00
(52) U.S. Cl. ..................... 604/523; 604/264; 604/164.09
(58) Field of Search ........................... 604/164, 167, 604/264, 523, 533–535, 539; 606/191, 194, 200

(56) References Cited

U.S. PATENT DOCUMENTS

| | | | |
|---|---|---|---|
| 5,496,310 | * 3/1996 | Exconde et al. ........................ | 606/205 |
| 5,846,260 | 12/1998 | Maahs ..................................... | 606/200 |
| 5,876,367 | 3/1999 | Kaganov et al. ......................... | 604/8 |
| 5,928,192 | 7/1999 | Maahs ..................................... | 604/96 |
| 5,989,281 | 12/1999 | Barbut et al. ........................... | 606/200 |
| 6,007,523 | 12/1999 | Mangosong ............................ | 604/284 |
| 6,007,557 | 12/1999 | Ambrisco et al. ..................... | 606/200 |
| 6,042,563 | * 3/2000 | Morejohn et al. ..................... | 604/96 |

* cited by examiner

Primary Examiner—Richard K. Seidel
Assistant Examiner—Michael J Hayes
(74) Attorney, Agent, or Firm—Lyon & Lyon LLP

(57) ABSTRACT

Modular systems comprising a cannula and at least one clip-on access port adjacent to a distal end of the cannula to provide insertion of one or more therapeutic or diagnostic devices into a vessel or cardiac tissue through a single incision site. The access port can be removably attached to a distal region of the cannula in a fixed orientation or in any desired orientation. The devices can be operated in combination or independently. The systems can be employed to provide multiple therapies, including blood perfusion, filtration, aspiration, vessel occlusion, atherectomy, and endoscopic devices. Methods of using the system for vessel cannulation are also disclosed herein.

34 Claims, 15 Drawing Sheets

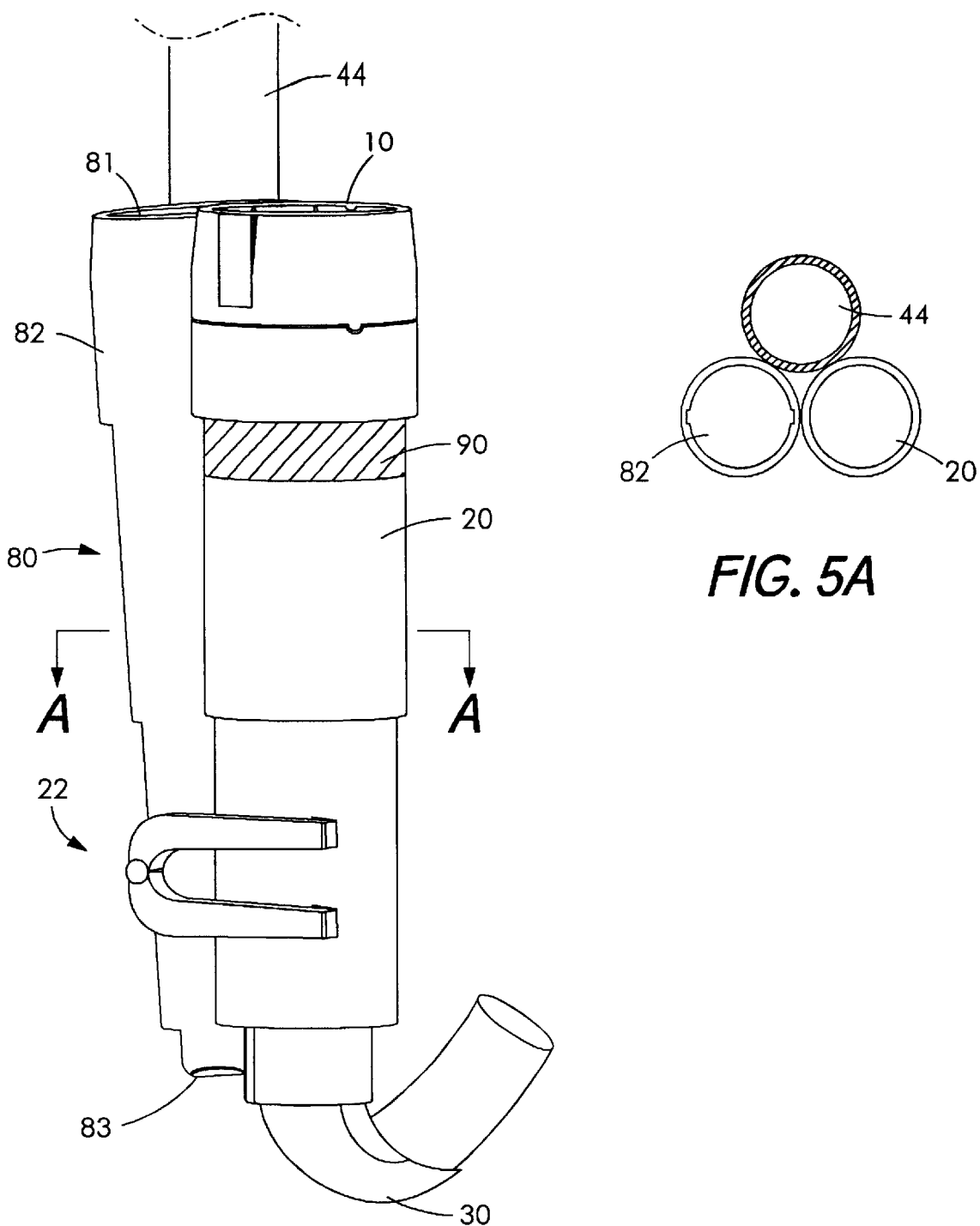
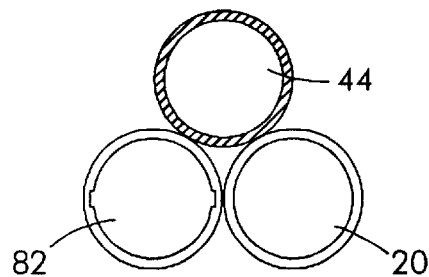
FIG. 5A
FIG. 5

CLIP-ON ACCESS PORT AND METHODS OF USE

FIELD OF THE INVENTION

The present invention relates generally to a modular system for introducing therapeutic or diagnostic devices, such as a blood filter, occluder, atherectomy device, stents, angiographic catheters, and pressure monitors to a vessel or cardiac tissue. More particularly, the system delivers the devices independently or in combination through a single incision on the vessel or cardiac tissue via one or more removably attached access ports and lumens.

BACKGROUND OF THE INVENTION

During various cardiothoracic, pulmonary, and vascular surgeries, including coronary artery bypass grafting, heart valve repair or replacement, atrial or ventricular septal defect repair, angioplasty, atherectomy, aneurysm repair, and pulmonary thrombectomy, cannulation of a patient's vessel (s) are often required to provide vascular access for delivery of various diagnostic and therapeutic devices. In a conventional approach, separate incisions are needed for introduction of each medical device. For example, during coronary artery bypass grafting (CABG) surgeries, cardiopulmonary bypass is established by cannulation of the aorta to provide circulatory isolation of the heart and coronary blood vessels. Two incisions on the aorta may be required, i.e., one for insertion of the arterial cannula and another for insertion of a balloon occluder to provide coronary isolation from the peripheral vascular system. When cardiac arrest is desired, a third incision may be required on the aorta to introduce a catheter for delivering cardioplegic solution to the coronary arteries. Additional incisions may be required for insertion of other devices, such as a blood filter, pressure monitor, or atherectomy device. Once the incisions are made on the aorta, the devices often remain in the aorta throughout the entire procedure despite only being used intermittently, e.g., the cardioplegia catheter.

Due to significant mortality and morbidity associated with conventional CABG surgeries from the use of cardiopulmonary bypass for circulatory support and the traditional method of access by median sternotomy, minimally invasive concepts recently have been adopted to make cardiothoracic procedures less invasive. Minimally invasive alternatives include the minimally invasive direct CABG procedure in which the operation is performed through minimal access incisions, eliminating cardiopulmonary bypass. The second alternative is to perform the procedure through minimal access incisions, and cardiopulmonary support is instituted through an extra thoracic approach, i.e., the port access approach. The third alternative is to perform the procedure on a beating heart which allows greater access for more extensive revascularization, i.e., the "off pump" sternotomy approach. In any of the minimally invasive alternatives, the space allowed for multiple instrumentation and device insertion is limited.

The disadvantages associated with the conventional or minimally invasive approach are that (1) by having multiple devices inserted in the aorta, the space available for the surgeon to perform procedures is limited, and (2) the aorta is traumatized as a result of multiple incisions, which may result in aortic dissection, aortic wall hematoma, and/or embolization of calcium plaque from the aortic wall. The greater the aortic trauma, the higher the perioperative morbidity a patient will endure.

New devices or systems are therefore needed which provide access to a patient's vessel and introduction of multiple diagnostic and therapeutic devices during cardiovascular procedures, thereby minimizing crowding caused by the multiple device insertions and trauma to the vessel wall.

SUMMARY OF THE INVENTION

The methods and systems of the present invention provide means of introducing a combination of multiple devices or instruments into a vessel through a single incision site, thereby reducing the number of incisions on the vessel and minimizing space crowding during vascular surgeries. More particularly, various devices and instruments can be inserted into the vessel through one or multiple lumens and access ports which are removably attached to a cannula in the modular access port systems, thereby minimizing the trauma of exchanging devices through the vessel wall. The methods and systems can be used in conventional or minimally invasive surgeries to provide any combination of the following functions: perfusion, drug delivery, fluid infusion, vessel occlusion, filtration, aspiration, blood sampling, venting, fluid diversion, venous return in cardiopulmonary bypass, atherectomy, fluid pumping, suturing, stapling, collagen or fibrin delivery, placement of pacing leads, use of angiographic catheters, angioplasty catheters, valvuloplasty catheters, electrode catheters, sizing tools, internal vessel segregating or isolating dams, endoscopic cameras, pressure monitors, shunts, stents, grafts, stent/grafts, vessel surfacing modalities, radioactive isotopes, graft delivery, and endoscopic devices. For example, devices traditionally introduced through the femoral artery (i.e., stents, atherectomy catheters, or angioplasty catheters) can also be introduced directly into the aorta, if deemed advantageous or beneficial to the patient.

In a first embodiment, the cannula has a lumen communicating between a proximal end and a distal end. The distal end is adapted for perfusion of blood, i.e. for use as an arterial cannula or venous return cannula in cardiopulmonary bypass. The proximal end is adapted for attachment to a bypass-oxygenator machine. A clip-on access port is removably attached to a distal region of the cannula. The access port has a lumen extending from a proximal end to a distal end. The proximal end of the port is adapted to receive medical devices. In certain embodiments, the access port can be attached to any standard arterial or venous cannula in any orientation. In other embodiments, the access port is attached to the cannula only in one orientation to ensure a desired relationship between the cannula and the access port.

In another embodiment, a second access port is removably mounted to the distal region of the cannula adjacent to the first access port, such that the ports are arranged at the vertices of a triangle. Having the triangular arrangement may be preferred in minimally invasive procedures where surgical space is limited. Alternatively, the second port is removably mounted to the first port, such that the ports and the cannula are arranged in a linear configuration. A hemostatic valve may be included in the lumen of either or both of the access ports. The distal ends of the cannula and/or the access ports may include a suture flange for securing the system onto the vessel.

In a first method to provide insertion of medical devices and cannulation of a vessel or cardiac tissue, the access port is attached adjacent the distal region of the cannula. The distal ends of the cannula and the access ports are inserted through an incision on the vascular or cardiac tissue. For example, to provide arterial cannulation for cardiopulmonary bypass, the cannula is inserted through an incision on the aorta. A medical device, such as a cardioplegia catheter, can be inserted through the proximal end of the access port and deployed in the aorta. When cardioplegia is no longer required, the catheter can be removed from the access port and another medical device, such as a pressure monitor can be inserted into the aorta through the port. In this way, the cannula system allows exchange of multiple devices through the access port without requiring additional incision.

In another method, when deployment of multiple medical devices into a vessel or cardiac tissue is necessary, a second access port can be attached to either the cannula or the first access port prior to inserting the cannula into the vascular tissue. For example, during arterial cannulation for cardiopulmonary bypass, a blood filter may be inserted through the first access port, and an occlusion catheter having a balloon occluder may be inserted through the second port into the aorta The blood filter is expanded to entrap embolic materials, calcium, myocardial tissue debris, or atheromatous plague, which arise as a result of introducing instrumentation or manipulating tissue during surgery. The balloon occluder is expanded to provide circulatory isolation of the coronary vessels from the peripheral vascular system. The proximal end of the cannula is attached to a bypass-oxygenator machine to deliver oxygenated blood to the aorta. After the cardiopulmonary bypass is established, a surgical procedure can be performed on the heart and/or aorta.

Alternatively, the blood filter and the occlusion catheter can be inserted sequentially through the access ports into the aorta. After completion of the surgical procedure, one or both devices can be removed from the access ports. In situations where continuation of the cardiopulmonary bypass is desired post-operatively due to a patient's low cardiac output state, the blood filter may be removed, leaving the occlusion catheter and the cannula in the aorta. In this manner, multiple therapies and procedures are employed in combination or independently of each other.

It will be understood that there are several advantages to using the clip-on access port(s) disclosed herein for delivering medical therapies. For example, the access port(s) (1) permit a combination of therapies to be employed through only one incision site, thereby minimizing trauma to the vessel wall, (2) allow multiple devices to be operated in combination or independently, (3) reduce the number of devices used concomitantly, thereby minimizing crowding in the surgical field, (4) can be employed in a variety of cardiac or vascular surgeries, (5) can be used in minimally invasive procedures, (6) can be easily mounted to a standard arterial or venous cannula and thereafter removed, and (7) can be mounted to a modified cannula, such that the port is attached to the cannula in only one orientation.

BRIEF DESCRIPTION OF THE DRAWINGS

FIG. 5 depicts a cannula with a second port adjacent the distal end of the cannula and adjacent the first port, wherein the ports are arranged at the vertices of a triangle.

FIG. 5A depicts a cross-section of the cannula of FIG. 5 through section line A—A.

DETAILED DESCRIPTION

Figure 1A:
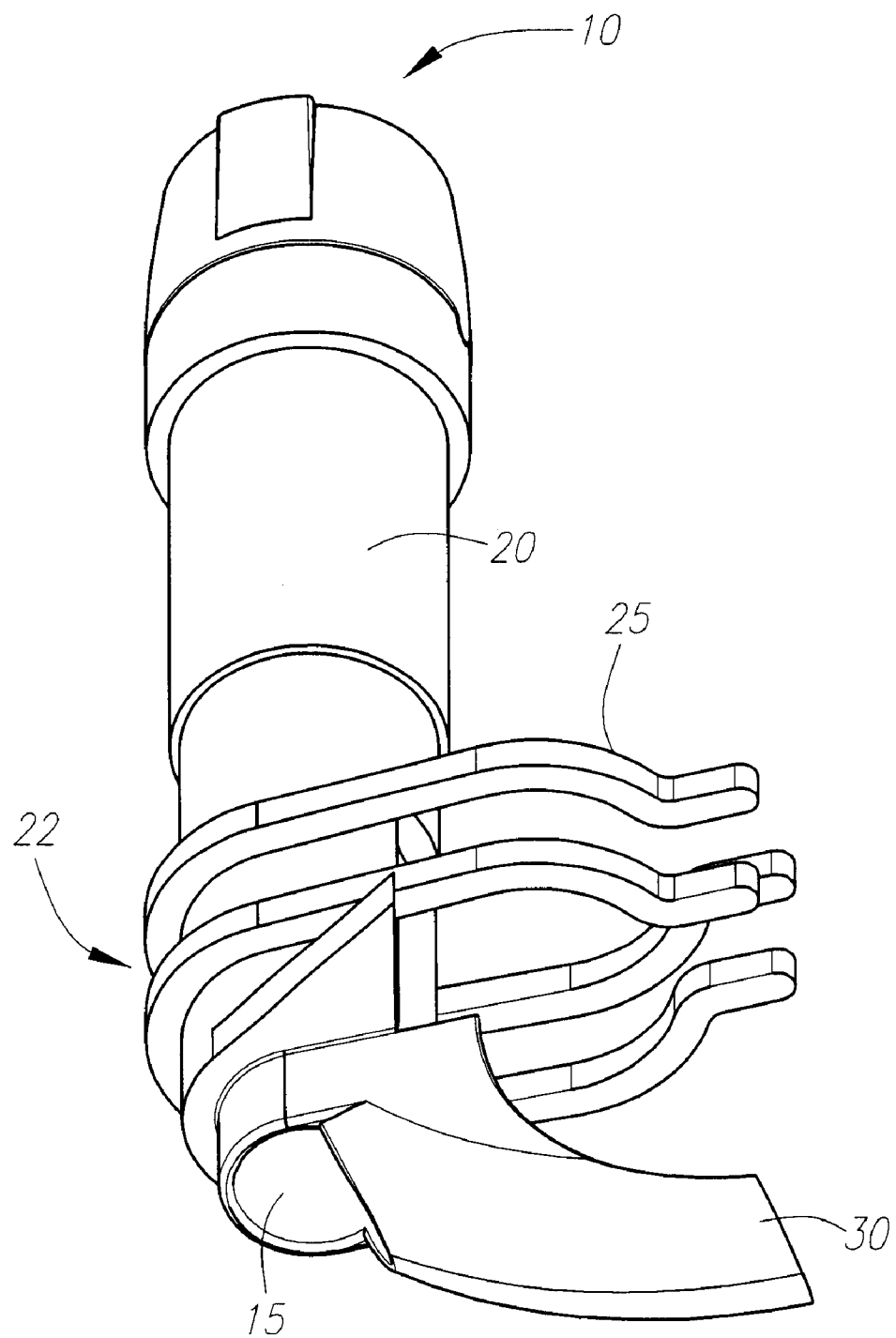
FIG. 1A depicts an oblique view of an embodiment of a clip-on access port according to the present invention.
Figure 1B:
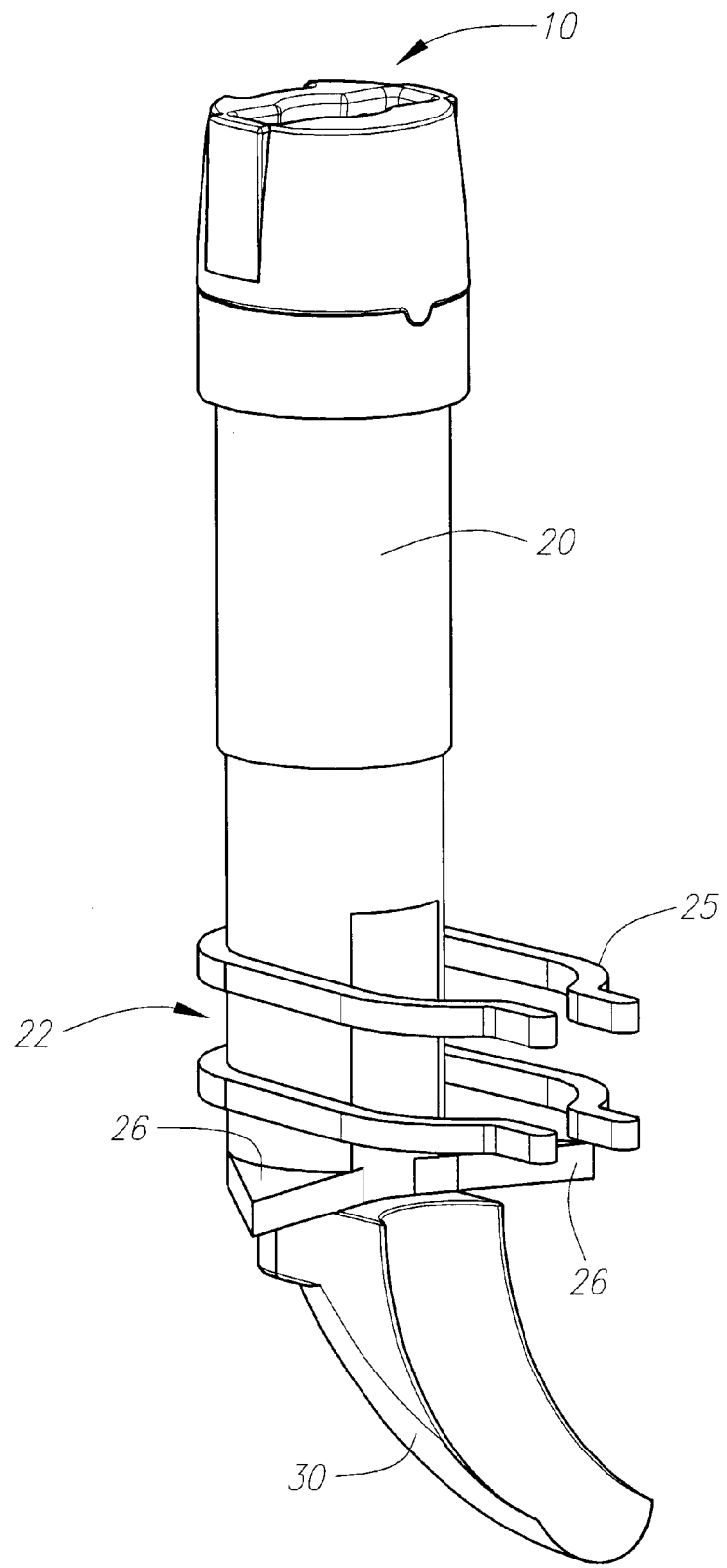
FIG. 1B depicts a lateral view of the clip-on access port of FIG. 1A.

In a first embodiment, a clip-on access port for deployment of medical devices, including a blood filter, a balloon occluder, a pressure monitor, an endoscope, a windsock filter, a flow director, an atherectomy catheter, an aspiration/suction catheter, a cardioplegia catheter, a coronary stent, a graft, and a perfusion catheter, in a vessel or cardiac tissue is provided as depicted in FIGS. 1A and 1B. The access port comprises proximal end 10, distal end 15, and lumen 20. Proximal end 10, which may include a hemostatic valve, is adapted to receive a medical device. Attachment mechanism 25, shown as a plurality of opposed clips, is mounted on distal region 22 of the access port. The attachment mechanism is adapted to be removably attached to a distal region of a cannula. Flange 30 may be included adjacent the distal end of the access port. First and second aligning members 26, which are mounted on distal region 22, can engage a suture flange on the cannula. Flange 30 and aligning members 26 fit to ensure proper circumferential alignment and coupling between the access port and a cannula.

Figure 1C:
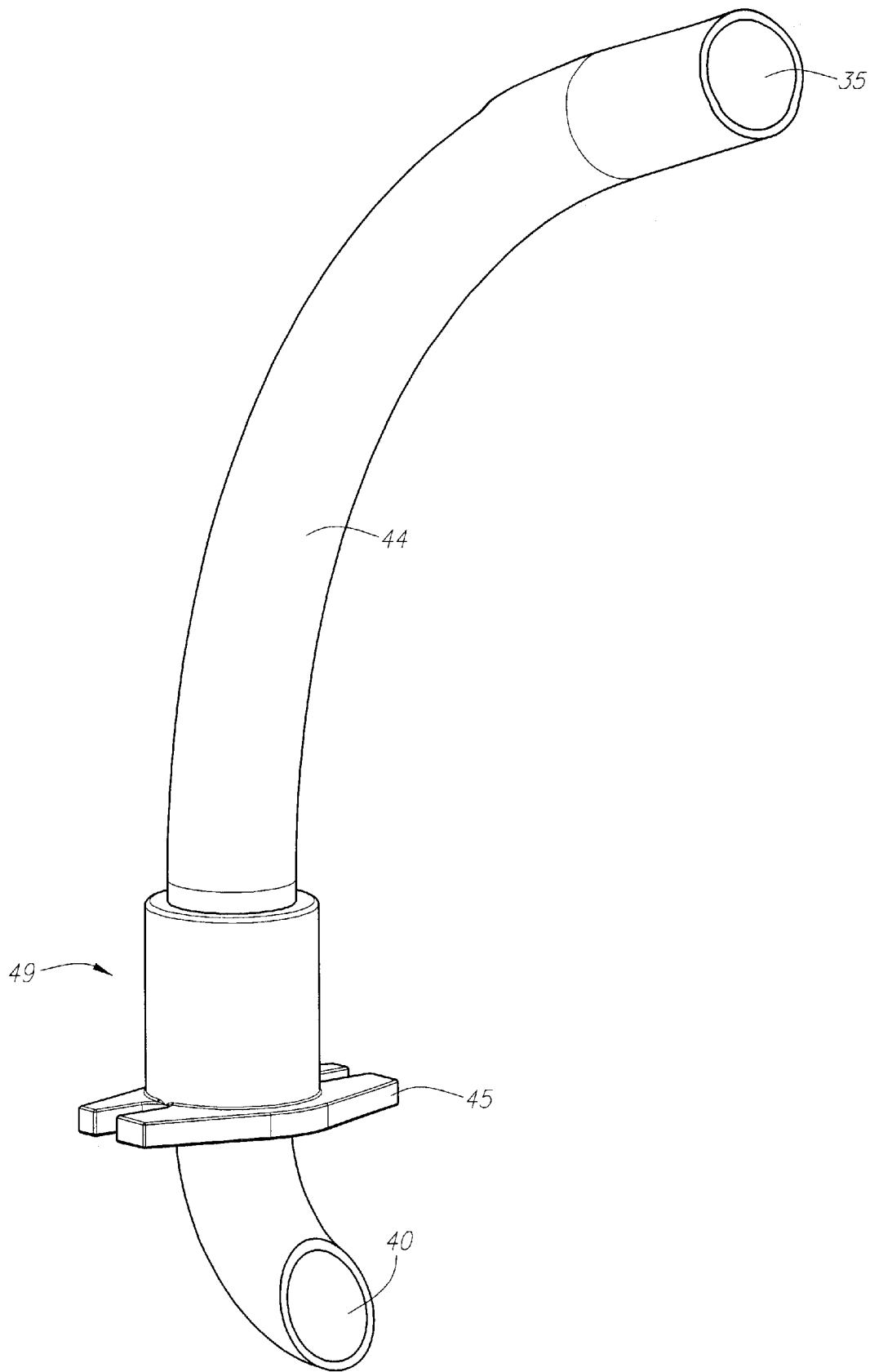
FIG. 1C depicts an embodiment of a cannula adapted for insertion into a vein or artery.

The access port described above can be removably attached to a standard arterial or venous cannula shown in FIG. 1C. The cannula has proximal end 35, distal end 40, and lumen 44. Suture flange 45 may be slideably mounted on distal region 49 of the cannula for securing the cannula onto the vascular tissue. Lumen 44 is adapted to receive oxygenated or deoxygenated blood. Proximal end 35 is adapted for attachment to a bypass-oxygenator machine.

Figure 1D:
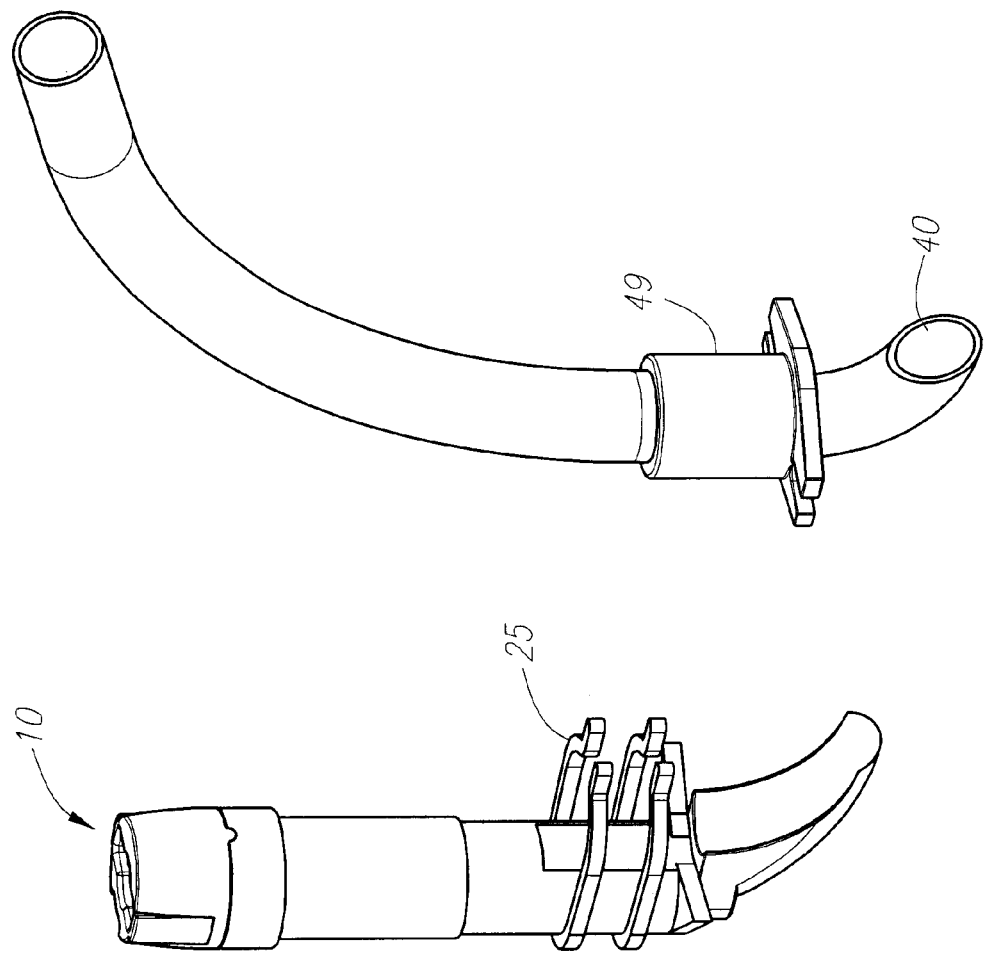
FIG. 1D depicts a spatial relationship between the access port of FIG. 1B and cannula of FIG. 1C.
Figure 1E:
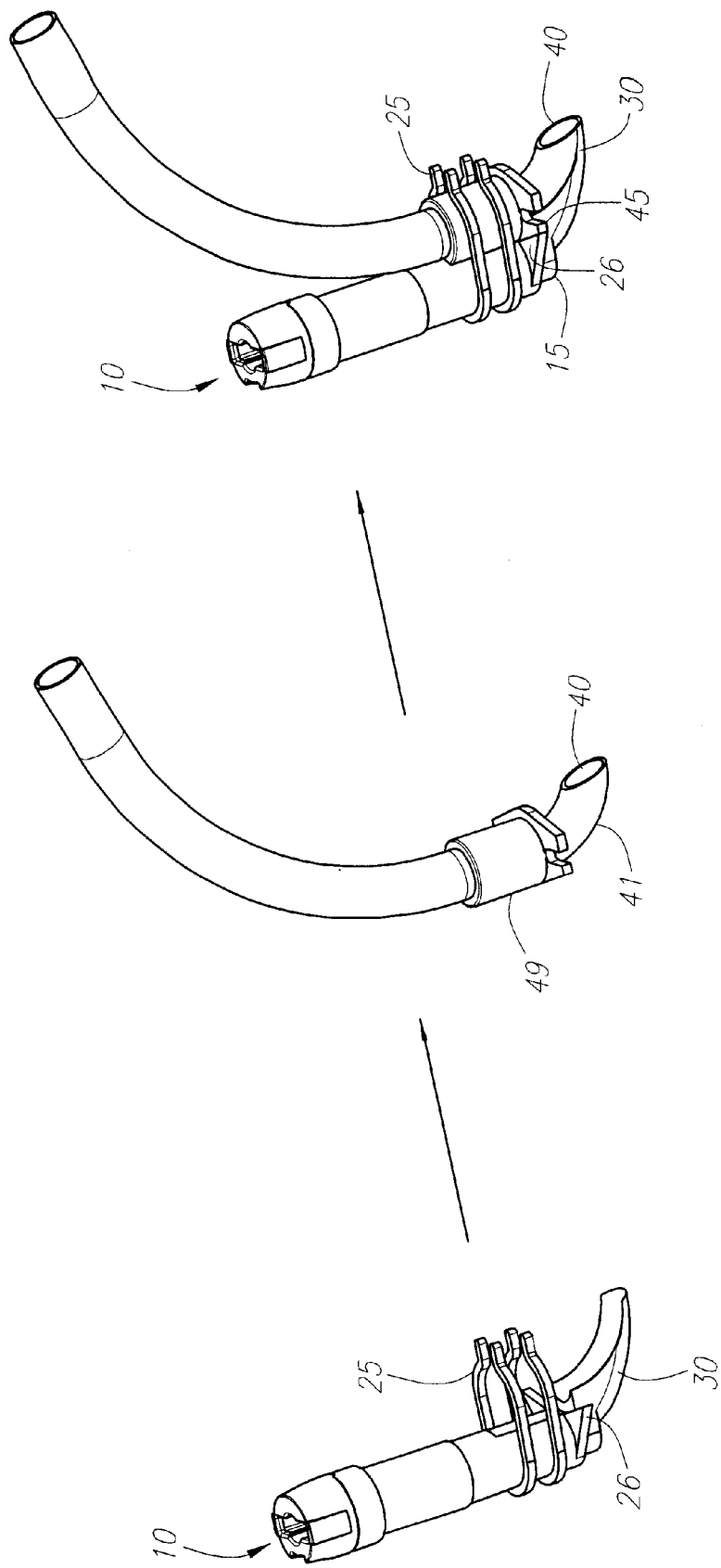
FIG. 1E depicts the access port of FIG. 1B attached to the cannula of FIG. 1C.

In use for cardiopulmonary bypass, for example, the access port is attached to distal region 49 of the cannula through attachment mechanism 25 in any preferred orientation as depicted in FIGS. 1D and 1E. In certain embodiments, the alignment will be fixed by a complementary fit between the clip-on port and the cannula, as by the engagement of opposing flat surfaces (e.g., aligning members 26 of the access port engages suture flange 45 of the cannula, and flange 30 of the access port engages distal region 41 of the cannula). After the access port is secured onto the cannula, distal end 40 of the cannula is inserted through an incision on the aortic wall into the ascending aorta. Various medical devices can then be inserted through proximal end 10 and passed through distal port 15 of the access port to deploy in the aorta.

Figure 1G:
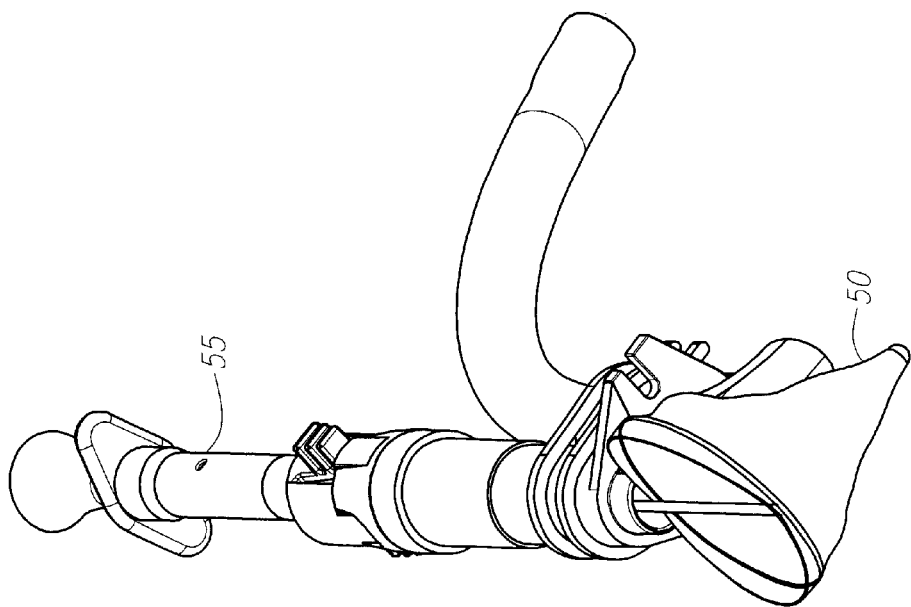
FIG. 1G depicts a distal view of the blood filter of FIG. 1F.
Figure 1F:
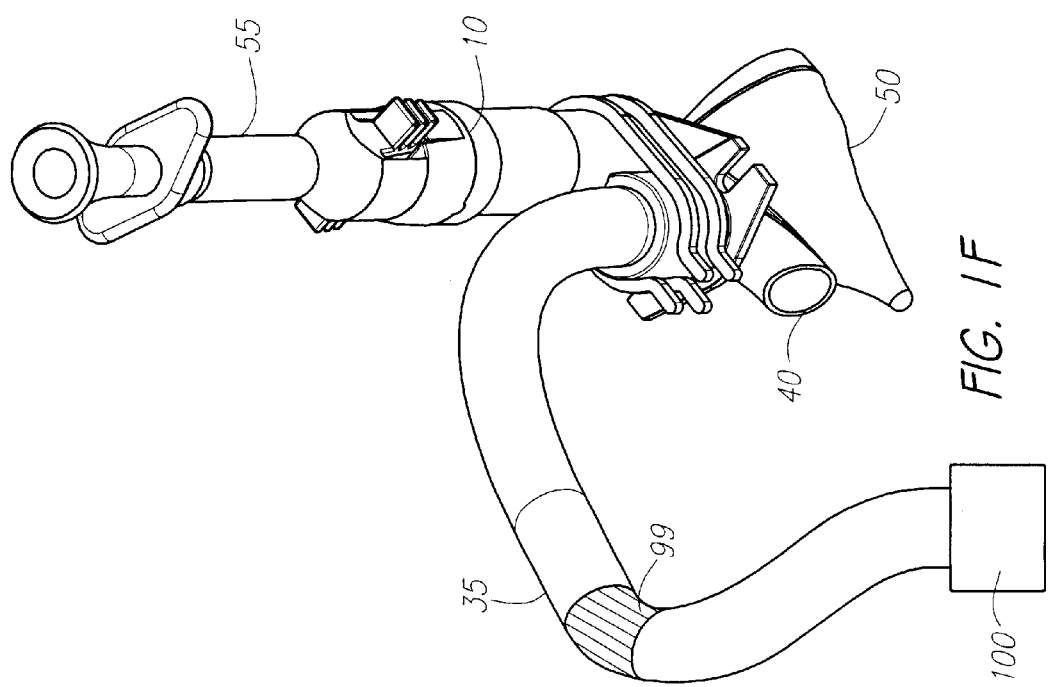
FIG. 1F depicts a blood filter inserted through the access port of FIG. 1E.

In FIGS. 1F and 1G, a blood filter device carrying filter 50 is inserted into proximal end 10 of the access port. The filter device includes plunger 55, which upon activation deploys filter 50 through port 15 of the access port. Filter 50 is shown in an expanded state. The reader is referred to Barbut et al., U.S. Pat. No. 5,769,816, Maahs, U.S. Pat. No. 5,846,260, Tsugita et al., U.S. Pat. No. 5,911,734, and Barbut et al., U.S. Pat. No. 5,662,671 (all of which are expressly incorporated herein by reference in their entirety), for a detailed description of the design and construction of blood filter devices. During cardiopulmonary bypass, oxygenated blood will be delivered to the aorta from proximal end 35, lumen 44 and distal port 40 of the cannula. Proximal end 35 is attached to a bypass-oxygenator machine 100 through connector 99. Expanded filter 50 captures embolic material, such as calcium deposits, atheromatous plaque, myocardial tissue debris, and thrombi, generated during cardiac surgery. Alternatively device 55 can be any of a balloon occluder, pressure monitor, endoscope, atherectomy device, aspirator, drug delivery catheter, blood-sampling device, valvuloplasty catheter, electrode catheter, segregating or isolating dams, endoscopic camera, or stent, graft, shunt, and perfusion catheters.

In certain embodiments, a second access port can be attached to the first access port or the cannula to provide deployment of other medical devices. For example, a catheter with a balloon occluder can be inserted into the second access port to provide circulatory isolation of the coronary and peripheral arteries. The catheter can also deliver carioplegia solution to arrest the heart. Alternatively, multiple ports will be bonded to form a single clip-on unit. In this way, the cannula system allows delivery of multiple medical therapies to the aorta through one incision, thereby minimizing trauma to the aortic wall.

Figure 2A:
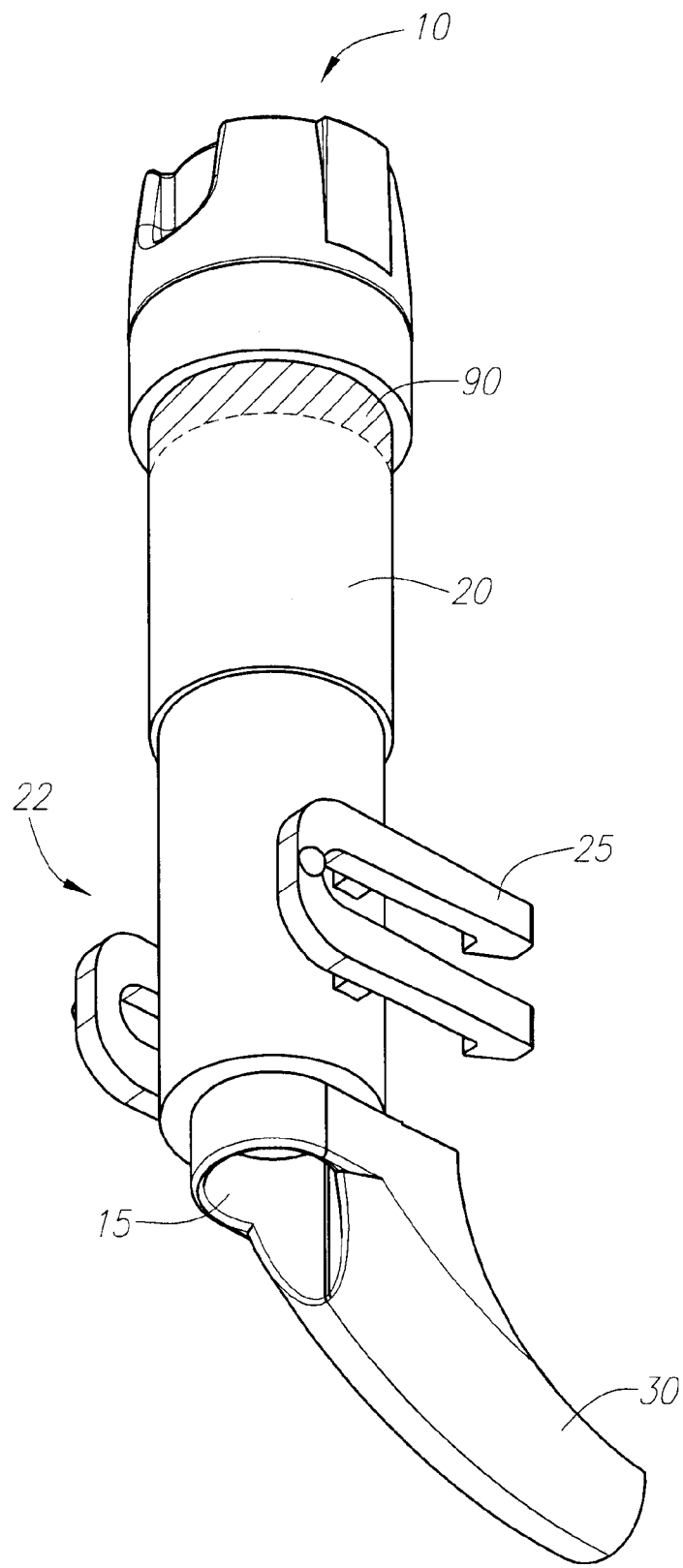
FIG. 2A depicts an oblique view of another embodiment of the clip-on access port.
Figure 2B:
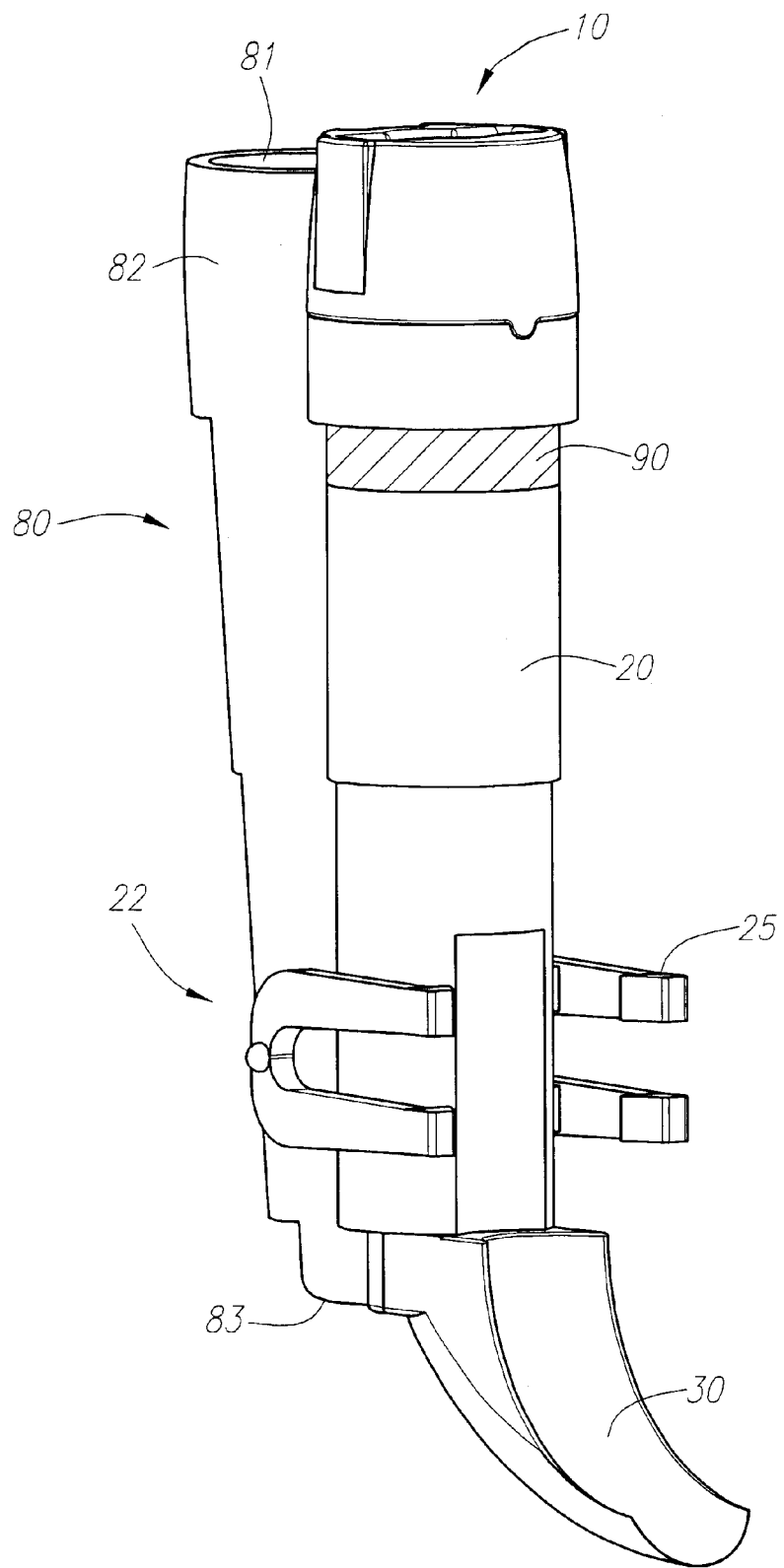
FIG. 2B depicts a lateral view of the access port of FIG. 2A.

FIGS. 2A and 2B depict another embodiment of the access port, which comprises proximal end 10, distal end 15, and lumen 20. Proximal end 10, which includes hemostatic valve 90, is adapted to receive a medical device. Attachment mechanism 25, mounted on distal region 22 of the access port, is adapted to engage a distal region of the cannula in a specific orientation. Extension member 30 is mounted on distal end 15 of the access port to ensure proper attachment to a cannula. In an alternative embodiment, the access port may include a second port 80 adjacent the first port, including proximal opening 81, lumen 82, and distal port 83.

Figure 2C:
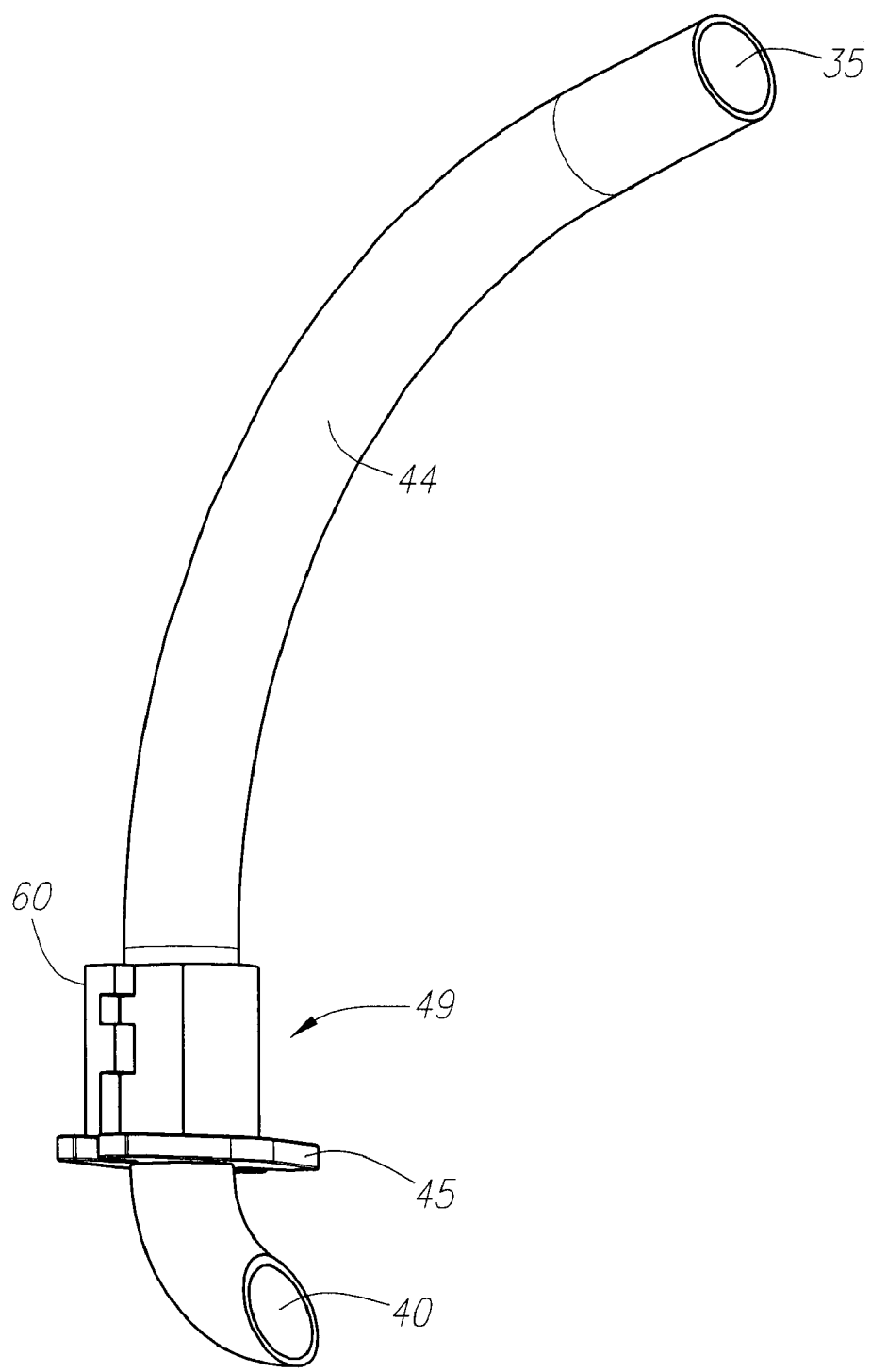
FIG. 2C depicts another embodiment of the cannula having a mounting mechanism at its distal region.

Another embodiment of the cannula, which is modified to accommodate the attachment of the access port, is shown in FIG. 2C. The cannula has proximal end 35, distal end 40, and lumen 44. Suture flange 45 may be slideably mounted on distal region 49 of the cannula for securing the cannula onto the vascular tissue. Lumen 44 is adapted to receive oxygenated or deoxygenated blood. Proximal end 35 is adapted for attachment to a bypass-oxygenator machine. Housing 60, which provides a complementary fit for the attachment mechanism of the access port, is mounted on distal region 49 of the cannula.

Figure 2D:
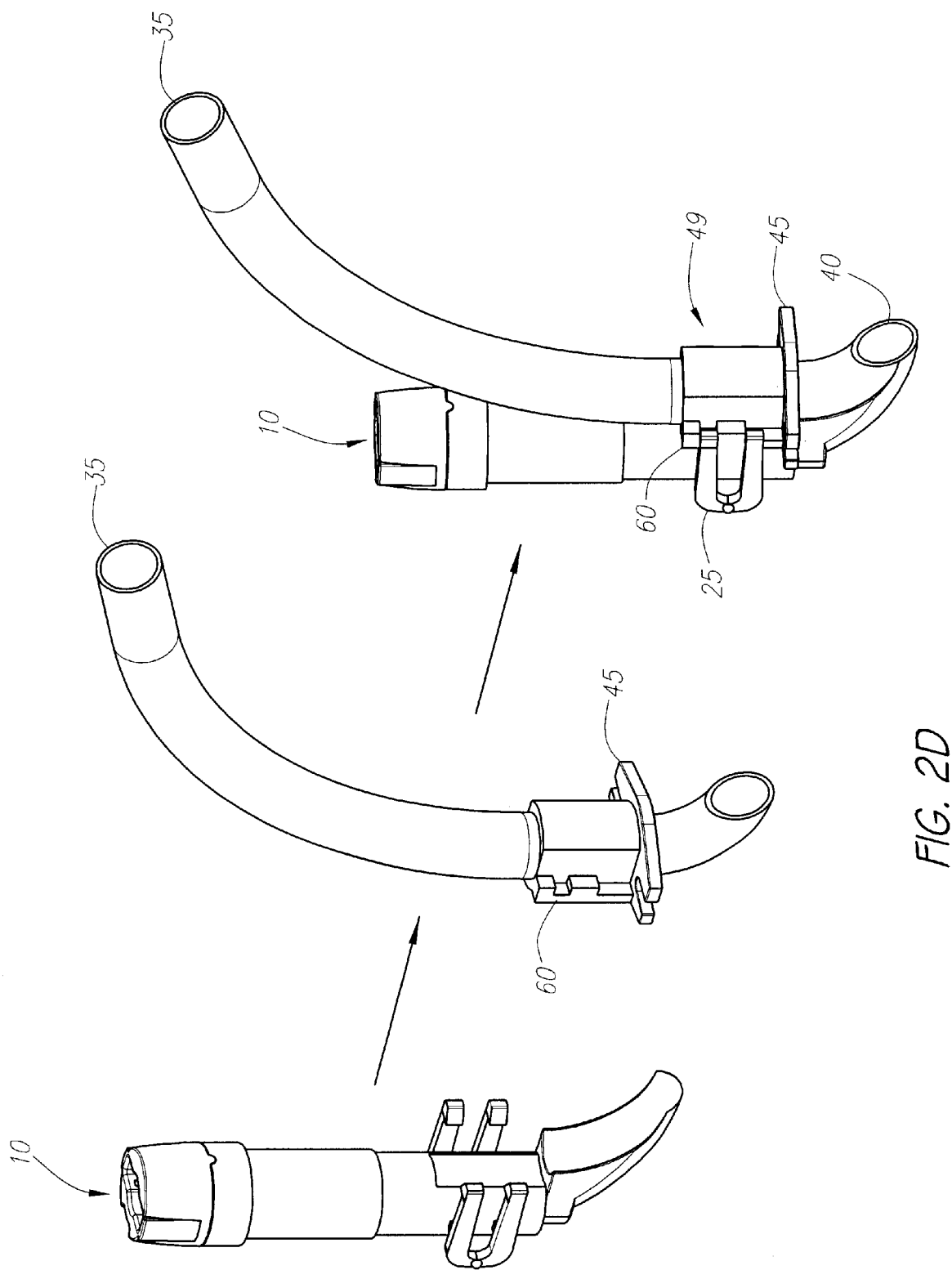
FIG. 2D depicts the access port of FIG. 2B attached to the distal region of the cannula of FIG. 2C in a predetermined orientation.

In use, the access port is attached to distal region 49 of the cannula through engaging attachment mechanism 25 with housing 60 in a fixed orientation as depicted in FIG. 2D. After the access port is secured onto the cannula, distal end 40 of the cannula is inserted through the vascular or cardiac tissue of interest. Sutures can be placed on suture flange 45 to secure the cannula onto the vascular tissue. Various medical devices can then be deployed by inserting through proximal end 10 and passing through distal port 15 of the access port. Having the access port attached to the cannula in one orientation may be preferred in situations where a specific direction of medical device deployment is required.

Figure 3A:
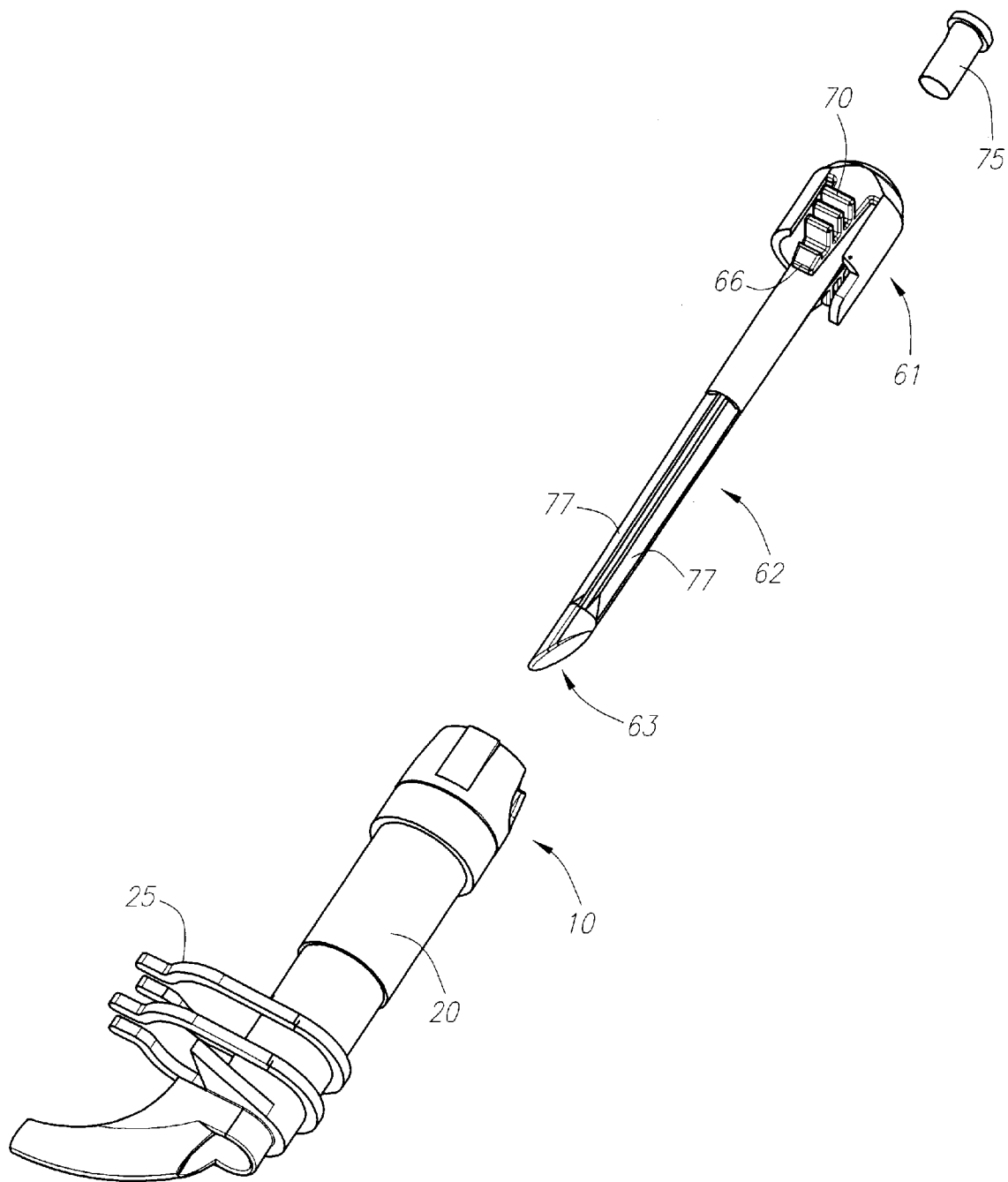
FIG. 3A depicts an obturator adapted for insertion into the access port of FIG. 1A.
Figure 3B:
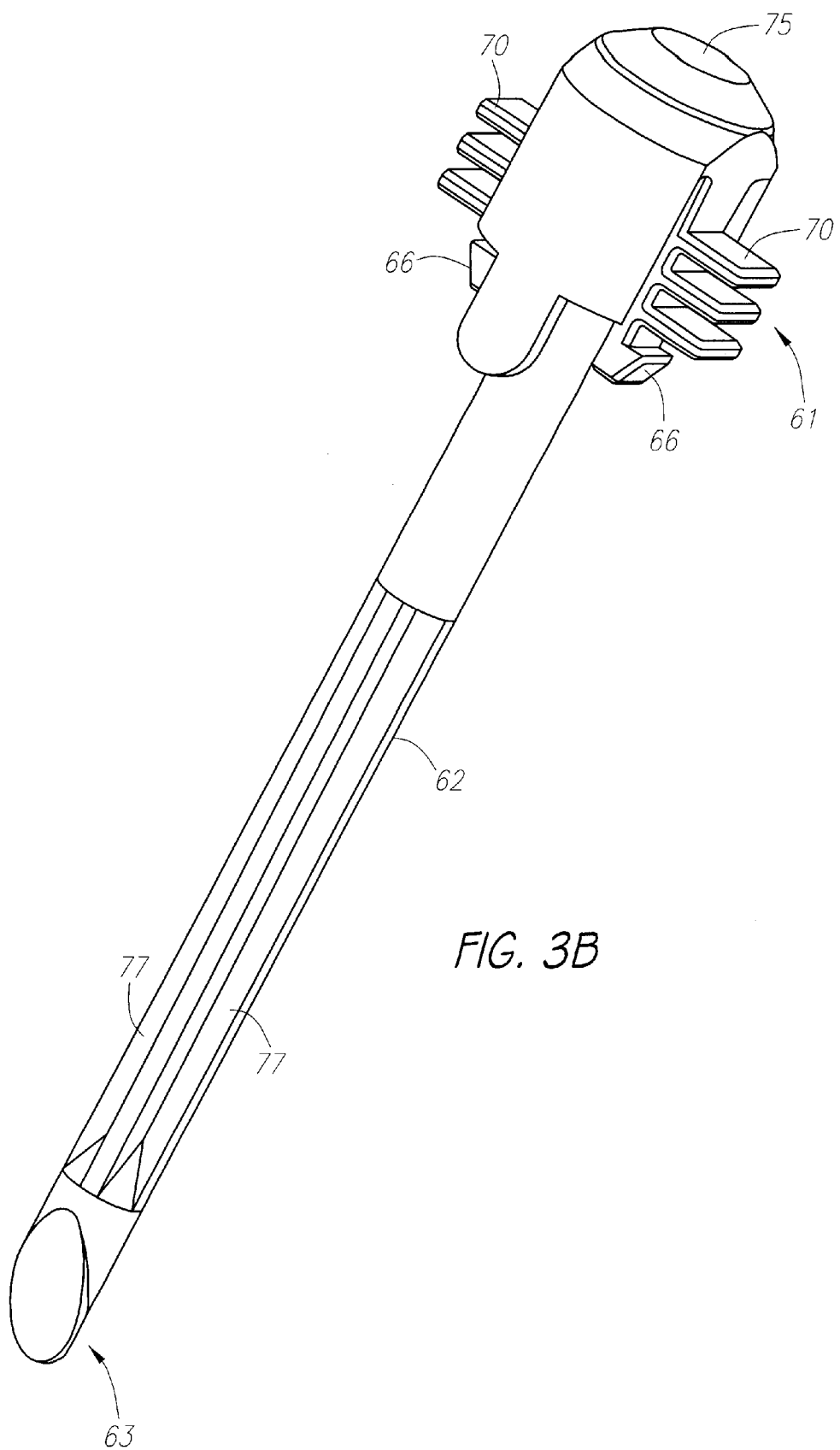
FIG. 3B depicts a lateral view of the obturator of FIG. 3A.
Figure 3C:
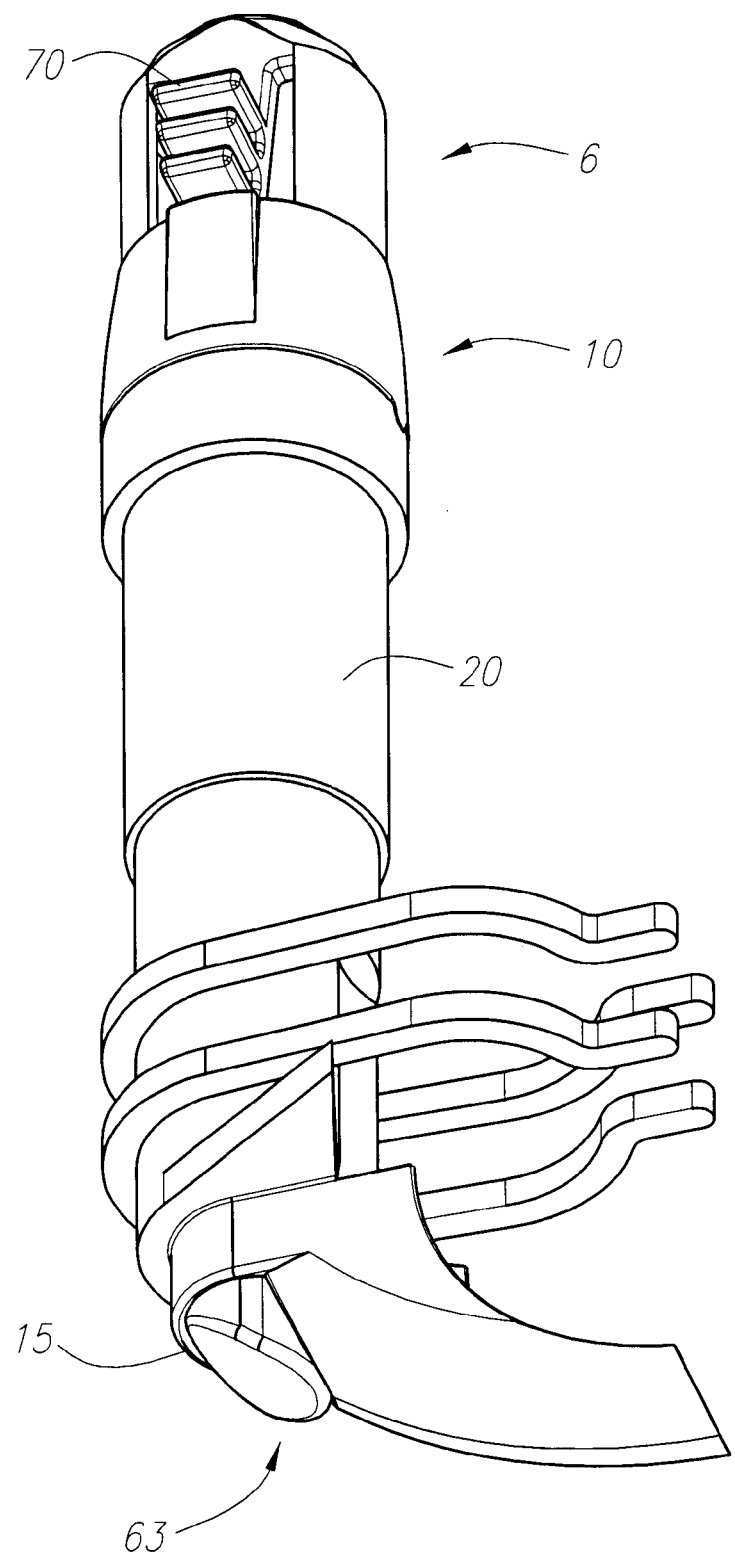
FIG. 3C depicts the access port of FIG. 3A having the obturator of FIG. 3B inserted through its lumen.
Figures 4, 4A:
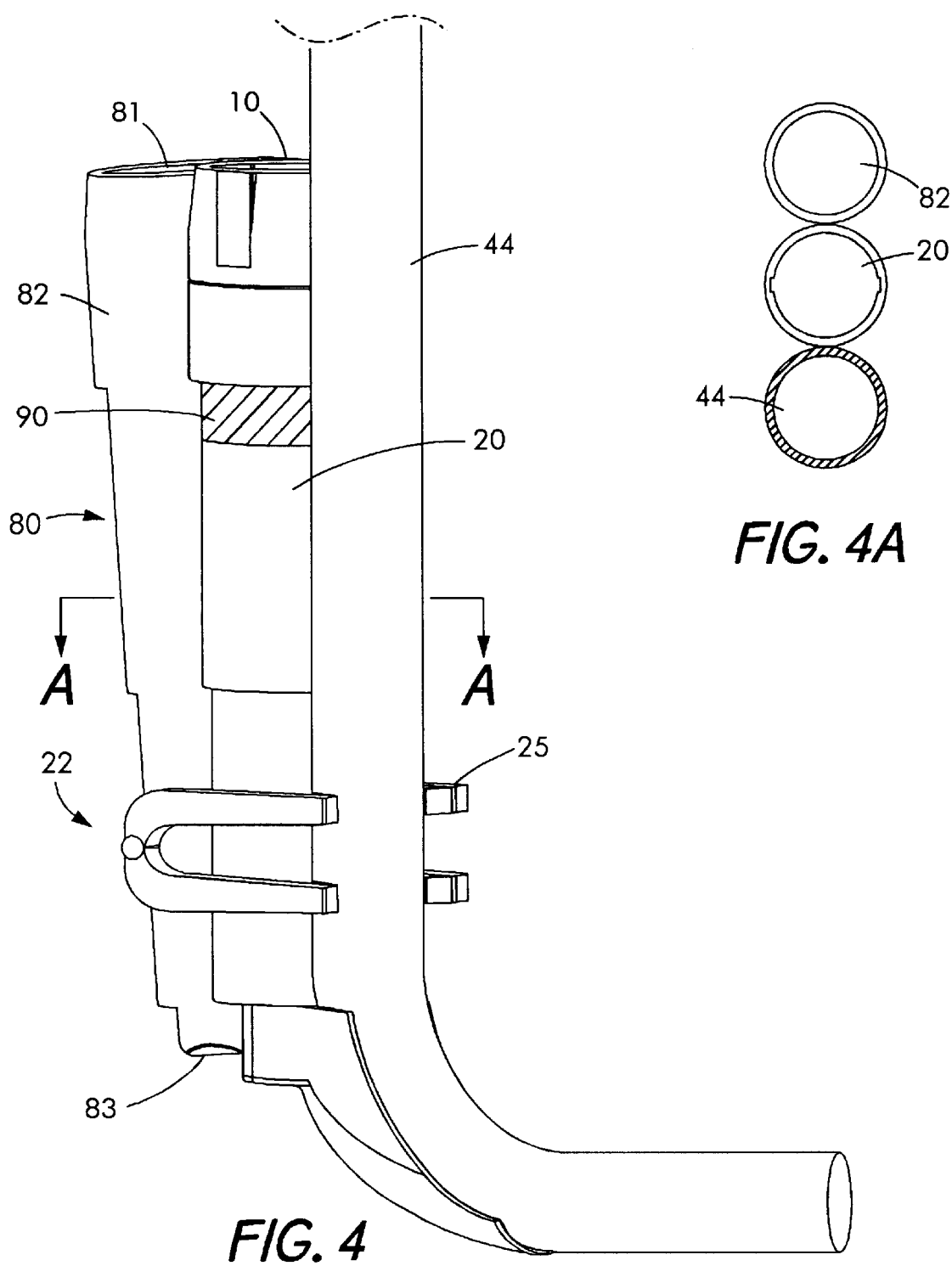
FIG. 4 depicts a cannula with a second port adjacent the distal end of the cannula and adjacent the first port, wherein the ports and the distal end of the cannula are arranged substantially in a line.
FIG. 4A depicts a cross-section of the cannula of FIG. 4 through section line A—A.

In certain embodiments, the access port includes an obturator adapted for insertion in proximal end 10 and lumen 20 of the access port as depicted in FIGS. 3A, 3B, and 3C. The obturator has proximal end 61, body 62, and distal end 63. Proximal end 61 includes releasable engaging mechanism 66 (snap cap), depicted as a latch in FIGS. 3A and 3B. Gripping members 70 are mounted proximal to the engaging mechanism 66 on opposite sides of the obturator. The engaging mechanism is operated by depressing the gripping members radially inward for insertion into the access port. Proximal end 61 also includes porous plug 75, which allows passage of air or gas, but not fluid or blood. Body 62 of the obturator has longitudinal grooves 77, which communicate with porous plug 75 and provide passage for air or gas.

In use, the obturator is inserted through proximal end 10 and lumen 20 of the access port as depicted in FIG. 3C. Distal end 63 of the obturator protrudes distal to port 15. The access port is then clipped onto a cannula and inserted into a vascular structure of interest. When the access port is not in use, the obturator can remain inserted to prevent back flow of blood or fluid. Porous plug 75 allows venting of air or gas and not blood or fluid. When insertion of a medical device is desired, the obturator is removed by depressing gripping members 70 radially inward to release engaging members 66 from proximal end 10 of the access port, and withdrawing the obturator from the access port.

The length of the cannula will generally be between 10 and 60 centimeters, more preferably approximately 20 to 35 centimeters, more preferably approximately 30 centimeters. The inner diameter of the cannula will generally be between 0.5 and 1.5 centimeters, preferably approximately 1.0 centimeters. The length of the clip-on access port will generally be between 2.0 and 10.0 centimeters, preferably approximately 6.0 centimeters. The inner diameter of the lumen of the access port will generally be between 0.2 and 1.2 centimeters, preferably approximately 0.6 centimeters. The foregoing ranges are set forth solely for the purpose of illustrating typical device dimensions. The actual dimensions of a device constructed according to the principles of the present invention may obviously vary outside of the listed ranges without departing from those basic principles.

Thus, while the invention has been described in connection with what is presently considered to be the most practical embodiment, it is to be understood that the invention is not to be limited to the disclosed embodiment, but on the contrary, is intended to cover various modifications and equivalent arrangements included within the spirit and scope of the appended claims.

What is claimed is:

1. A cannula for cardiopulmonary bypass, comprising:
    an elongate tubular member having a proximal end, a distal end, and a lumen extending from the proximal to the distal end;
    a clip to hold a removably attached port adjacent the distal end of the cannula, said port having a proximal end adapted to receive a medical device, a distal end, and a lumen therebetween;

a medical device inserted through the port and passing through cardiac tissue into a lumen or body cavity.

2. The cannula of claim 1, further comprising a second port adjacent the first port at the distal end of the cannula, said second port having a proximal end adapted to receive a medical device, a distal end, and a lumen therebetween.

3. The cannula of claim 1, wherein the medical device is a blood filter.

4. The cannula of claim 1, wherein the medical device is a balloon occluder.

5. The cannula of claim 1, wherein the medical device is a pressure monitor.

6. The cannula of claim 1, wherein the medical device is an endoscope.

7. The cannula of claim 1, wherein the medical device is an atherectomy device.

8. The cannula of claim 1, wherein the medical device is an aspirator.

9. The cannula of claim 1, wherein the medical device is a drug delivery catheter.

10. The cannula of claim 1, wherein the medical device is a blood-sampling device.

11. The cannula of claim 10, wherein the blood-sampling device obtains blood for analyzing activated clotting time.

12. The cannula of claim 1, further comprising a second port adjacent the distal end of the cannula and adjacent the first port, wherein the ports are arranged at the vertices of a triangle.

13. The cannula of claim 1, further comprising a second port adjacent the distal end of the cannula and adjacent the first port, wherein the ports and the distal end of the cannula are arranged substantially in a line.

14. The system of claim 1, wherein the proximal end of the tubular member is adapted for attachment to a bypass oxygenator machine.

15. The cannula of claim 1, wherein the medical device is selected from the group consisting of a blood filter, an occlusion catheter, an aspirator, an angioplasty catheter, a valvuloplasty catheter, an electrode catheter, internal vessel segregating or isolating dams, an endoscopic camera, a pressure monitor, a stent, a graft, a stent-graft, a shunt, a perfusion catheter, and endoscopic devices.

16. The cannula of claim 1, wherein the elongate tubular member is flexible.

17. The cannula of claim 1, wherein the first and the second ports further include hemostatic valves in their lumens.

18. The cannula of claim 1, wherein the cannula further includes a suture flange.

19. The cannula of claim 1, wherein the clip comprises one or more member that extend between the cannula and the port.

20. A method for cannulation of a patient's blood vessel or cardiac tissue, comprising the steps of:
providing a cannula having a lumen;
attaching a removable port adjacent a distal end of the cannula by operating a clip;
inserting the distal end of the cannula and adjacent port into a blood vessel or cardiac tissue;
inserting a medical device through the port into the vessel or cardiac tissue; and
deploying the medical device.

21. The method of claim 20, further comprising the steps of:
inserting a second medical device through the port into the vessel or cardiac tissue; and
deploying the second medical device.

22. The method of claim 20, wherein the clip comprises one or more member that extend between the cannula and the port.

23. The method of claim 20, wherein the first medical device is selected from the group consisting of a blood filter, an occlusion catheter, an aspirator, an angioplasty catheter, a valvuloplasty catheter, an electrode catheter, internal vessel segregating or isolating dams, an endoscopic camera, a pressure monitor, a stent, a graft, a stent-graft, a shunt, a perfusion catheter, and endoscopic devices.

24. The method of claim 20, wherein the vessel is an artery.

25. The method of claim 22, wherein the artery is the aorta.

26. The method of claim 20, wherein the cardiac tissue is the right atrium.

27. The method of claim 20, wherein the vessel is a vein.

28. The method of claim 20, wherein the vessel is the inferior vena cava.

29. The method of claim 20, further comprising the step of infusing blood through the lumen of the cannula.

30. The method of claim 20, wherein the second medical device is selected from the group consisting of a blood filter, an occlusion catheter, an aspirator, an angioplasty catheter, a valvuloplasty catheter, an electrode catheter, internal vessel segregating or isolating dams, an endoscopic camera, a pressure monitor, a stent, a graft, a stent-graft, a shunt, a perfusion catheter, and endoscopic devices.

31. The method of claim 20, further comprising the steps of:
attaching a second port adjacent the distal end of the cannula; and
inserting a second medical device through the second port into the vessel or cardiac tissue.

32. The method of claim 20, further comprising the steps of inserting an obturator through the port.

33. The method of claim 32, wherein the obturator includes a porous plug.

34. The method of claim 31, wherein the second medical device is selected from the group consisting of a blood filter, an occlusion catheter, an aspirator, an angioplasty catheter, a valvuloplasty catheter, an electrode catheter, internal vessel segregating or isolating dams, an endoscopic camera, a pressure monitor, a stent, a graft, a stent-graft, a shunt, a perfusion catheter, and endoscopic devices.

* * * * *